(12) United States Patent
Van Heumen

(10) Patent No.: US 9,814,126 B2
(45) Date of Patent: Nov. 7, 2017

(54) PHOTON SOURCE, METROLOGY APPARATUS, LITHOGRAPHIC SYSTEM AND DEVICE MANUFACTURING METHOD

(71) Applicant: ASML Netherlands B.V., Veldhoven (NL)

(72) Inventor: Martijn Petrus Christianus Van Heumen, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/029,285

(22) PCT Filed: Sep. 23, 2014

(86) PCT No.: PCT/EP2014/070200
§ 371 (c)(1),
(2) Date: Apr. 14, 2016

(87) PCT Pub. No.: WO2015/055387
PCT Pub. Date: Apr. 23, 2015

(65) Prior Publication Data
US 2016/0255710 A1    Sep. 1, 2016

Related U.S. Application Data

(60) Provisional application No. 61/892,156, filed on Oct. 17, 2013.

(51) Int. Cl.
*G03F 7/20* (2006.01)
*H05H 1/24* (2006.01)
(Continued)

(52) U.S. Cl.
CPC ............... *H05H 1/24* (2013.01); *G01N 21/71* (2013.01); *G03F 7/70016* (2013.01);
(Continued)

(58) Field of Classification Search
CPC .. G01B 2210/56; G01N 21/71; G01N 21/956; G01N 2201/06113;
(Continued)

(56) References Cited

U.S. PATENT DOCUMENTS 4,049,987 A    9/1977  Helms
4,054,812 A    10/1977  Lessner et al.
(Continued)

FOREIGN PATENT DOCUMENTS

NL         8403294        6/1985
WO       WO 00/28575      5/2000
(Continued)

OTHER PUBLICATIONS

Written Opinion of the International Searching Authority With Search Report directed to App. No. PCT/EP2014/070200, dated Dec. 11, 2014; 10 pages.
(Continued)

*Primary Examiner* — Steven H Whitesell Gordon
(74) *Attorney, Agent, or Firm* — Sterne, Kessler, Goldstein & Fox P.L.L.C.

(57) ABSTRACT

A radiation driven light source comprises laser and focusing optics. These produce a beam of radiation focused on a plasma forming zone within a first container containing a gas (e.g. Xe). Collection optics collects photons emitted by a plasma maintained by the laser radiation to form a beam of output radiation. First container is enclosed within a hermetically sealed second container. Any ozone generated within the second container as a result of ultraviolet components of the output radiation is completely contained within the second container. Second container further filters out the ultraviolet components. Microwave radiation may be used instead of laser radiation to form the plasma.

26 Claims, 4 Drawing Sheets

(51) Int. Cl.
  *H01J 61/34* (2006.01)
  *H01J 61/40* (2006.01)
  *H01J 65/04* (2006.01)
  *G01N 21/71* (2006.01)
  *G01N 21/956* (2006.01)

(52) U.S. Cl.
  CPC ...... *G03F 7/70575* (2013.01); *G03F 7/70616* (2013.01); *G03F 7/70916* (2013.01); *H01J 61/34* (2013.01); *H01J 61/40* (2013.01); *H01J 65/04* (2013.01); *G01B 2210/56* (2013.01); *G01N 21/956* (2013.01); *G01N 2201/068* (2013.01); *G01N 2201/06113* (2013.01)

(58) Field of Classification Search
  CPC .......... G01N 2201/068; G03F 7/70016; G03F 7/70575; G03F 7/70616; G03F 7/70916; H01J 61/34; H01J 61/40; H01J 65/04; H01J 1/24
  See application file for complete search history.

(56) References Cited

U.S. PATENT DOCUMENTS

| | | | |
|---|---|---|---|
| 6,108,126 A | 8/2000 | Hagiwara et al. | |
| 8,415,866 B2 | 4/2013 | Jenek | |
| 2003/0117074 A1 | 6/2003 | Lapatovich et al. | |
| 2005/0031281 A1* | 2/2005 | Nath | G02B 6/0008 385/125 |
| 2007/0194683 A1 | 8/2007 | Serita et al. | |
| 2010/0164380 A1* | 7/2010 | Sumitomo | H01J 61/025 313/639 |
| 2011/0027704 A1 | 2/2011 | Cramer et al. | |
| 2011/0204265 A1 | 8/2011 | Smith et al. | |
| 2012/0044470 A1* | 2/2012 | Smilde | G03F 1/44 355/53 |
| 2012/0200216 A1 | 8/2012 | Okazaki et al. | |
| 2013/0181595 A1 | 7/2013 | Bezel et al. | |
| 2013/0329204 A1* | 12/2013 | Pellemans | H05H 1/24 355/67 |

FOREIGN PATENT DOCUMENTS

WO  WO 2009/078708 A1  6/2009
WO  WO 2009/106279 A1  9/2009

OTHER PUBLICATIONS

English-language Abstract for App. No. NL 8403294 A, dated Jun. 3, 1985; 1 page.

English-language Abstract for App. No. WO 0028575 A1, dated May 18, 2000; 1 page.

* cited by examiner

PHOTON SOURCE, METROLOGY APPARATUS, LITHOGRAPHIC SYSTEM AND DEVICE MANUFACTURING METHOD

CROSS-REFERENCE TO RELATED APPLICATIONS

This application claims the benefit of U.S. provisional application 61/892,156, which was filed on Oct. 17, 2013 and which is incorporated herein in its entirety by reference.

BACKGROUND

Field of the Invention

The present invention relates to plasma based photon sources. Such sources may be used for example to provide high brightness illumination in methods and for metrology usable, for example, in the manufacture of devices by lithographic techniques and to methods of manufacturing devices using lithographic techniques.

Background Art

Photon sources according to the invention may find application in a wide range of situations. As an example application, the following will describe use of the invention as a light source in metrology. As a particular field of application of metrology, the following shall refer for the sake of example to metrology in the manufacture of devices by lithography.

The terms 'light' and 'light source' may be used conveniently to refer to the generated radiation and the photon source itself, without implying any limitation to radiation of visible wavelengths.

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

These devices direct a beam of radiation onto a target and measure one or more properties of the scattered radiation. From these measured properties a property of interest of the target can be determined.

In one commercially available metrology apparatus, the light source is a xenon (Xe) arc-discharge lamp. Light from this lamp is imaged onto the measurement target through an illumination branch of the apparatus sensor, the last stage of which consists of a high-NA objective. The measurement spot may have a diameter of 25 µm, for example. The time required for each measurement depends in practice on the brightness of the light source at a given wavelength or wave range. Future generations of apparatus are desired to provide an increased spectral bandwidth and sensor design with lower transmittance, while keeping the measurement time the same or shorter. Significant source brightness improvements are necessary to fulfill these requirements.

Plasma-based photon sources, for example laser driven light sources (LDLS) offer higher brightnesses. Plasmas are generated in a gaseous medium by the application of energy through electric discharge, and laser energy. The spectral distribution of the radiation may be broadband or narrowband in nature, and wavelengths may be in the near infrared, visible and/or ultraviolet (UV) bands. Plasma can take an elongate form, which increases the radiating area and increases the brightness. Measures are described for reducing the longitudinal extent of the plasma, with the aim of increasing the brightness.

In applications using photon sources such as LDLS sources, the source in use may emit radiation of different wavelengths, including ultraviolet radiation. However, UV photons are related to issues such as ozone generation, chemical contamination and absorption. In applications where the UV radiation is not of use, these issues may be overcome by purging the system or by using ozone-free lamp types. The ozone-free lamp bulb is made of glass which absorbs UV light, preventing ozone generation. However, the lifetime of ozone-free lamps, in particular when used in LDLS applications, is shorter compared to lamps releasing UV light, due to the effect of solarization. In applications using lamps releasing UV, purging of the lamp housing or of the entire beam path is required to prevent ozone generation and/or remove generated ozone. Both scenarios consequently increase the cost of ownership/cost of goods CoO/CoG.

SUMMARY

In a first aspect of the invention there is provided a radiation produced plasma-based photon source apparatus comprising: a first container for containing a gaseous medium in which a plasma is generated following excitation by a driving radiation, and a second container enclosing the first container, wherein the radiation produced plasma-based photon source apparatus is operable to emit output radiation comprising a plurality of component wavelengths, the radiation further comprising an ultraviolet component; and the second container is hermetically sealed and operable to substantially remove the ultraviolet component from the output radiation The photon source may be applied in metrology, for example in lithography. The invention in another aspect provides method of measuring a property of structures that have been formed by a lithographic process on a substrate, the method comprising the steps of: illuminating structures using output radiation of a photon source according to the first aspect of the invention, set forth above; detecting radiation diffracted by the structures; and determining from properties of the diffracted radiation one or more properties of the structure The invention yet further provides an inspection apparatus for measuring a property of a structure on a substrate, the apparatus comprising: a support for the substrate having the structure thereon; an optical system for illuminating the structure under predetermined illumination conditions and for detecting predetermined portions of radiation diffracted by the component target structures under the illumination conditions; a processor arranged to process information characterizing the detected radiation to obtain a measurement of the property of the structure, wherein the optical system includes a photon source apparatus according to the invention as set forth above.

The invention yet further provides a lithographic system comprising: a lithographic apparatus comprising: an illumination optical system arranged to illuminate a pattern; a projection optical system arranged to project an image of the pattern onto a substrate; and an inspection apparatus according to an embodiment of the invention as set forth above, wherein the lithographic apparatus is arranged to use the measurement results from the inspection apparatus in applying the pattern to further substrates.

The invention yet further provides a method of manufacturing devices wherein a device pattern is applied to a series of substrates using a lithographic process, the method including inspecting at least one composite target structure formed as part of or beside the device pattern on at least one of the substrates using the aforementioned method of measuring a property of structures that have been formed by a lithographic process on a substrate, and controlling the lithographic process for later substrates in accordance with the result of the inspection method.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein

BRIEF DESCRIPTION OF THE DRAWINGS

Embodiments of the invention will now be described, by way of example only, with reference to the accompanying drawings in which.

Figure 1:
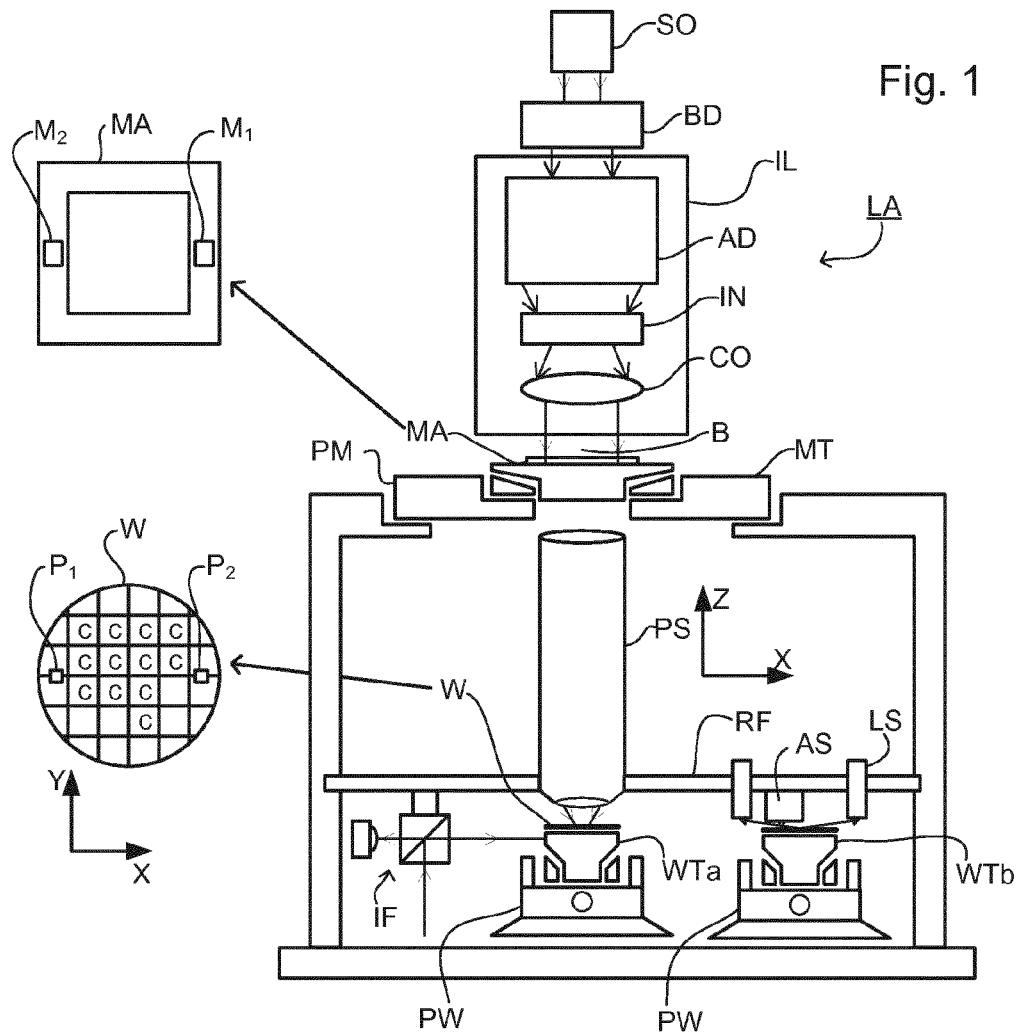
FIG. 1 depicts a lithographic apparatus according to an embodiment of the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF EXEMPLARY EMBODIMENT

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals, and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing embodiment of the invention in detail, it is instructive to present an example environment in which embodiments of the present invention may be implemented.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable minor arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small minors, each of which can be individually tilted so as to reflect an incoming radiation beam in different directions. The tilted mirrors impart a pattern in a radiation beam, which is reflected by the minor matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable minor array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers, is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable minor array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
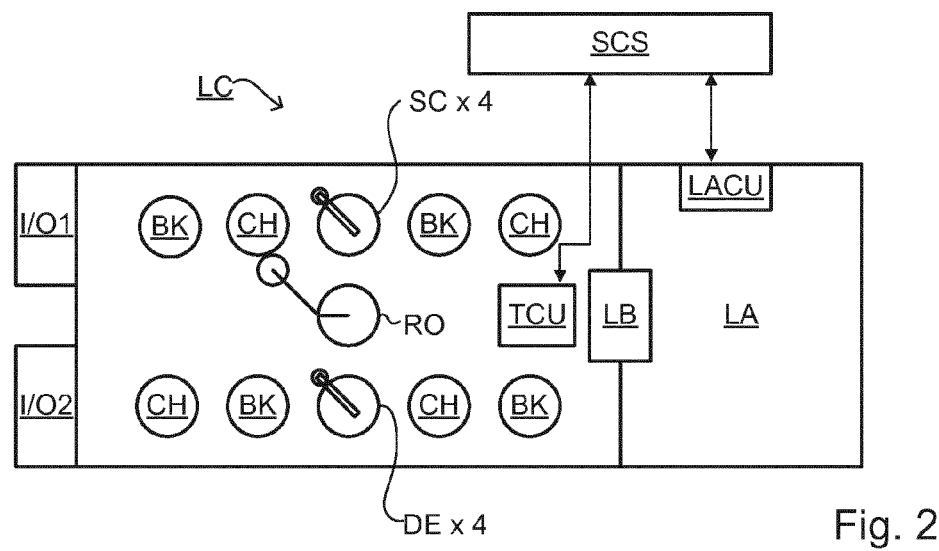
FIG. 2 depicts a lithographic cell or cluster according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Figure 3:
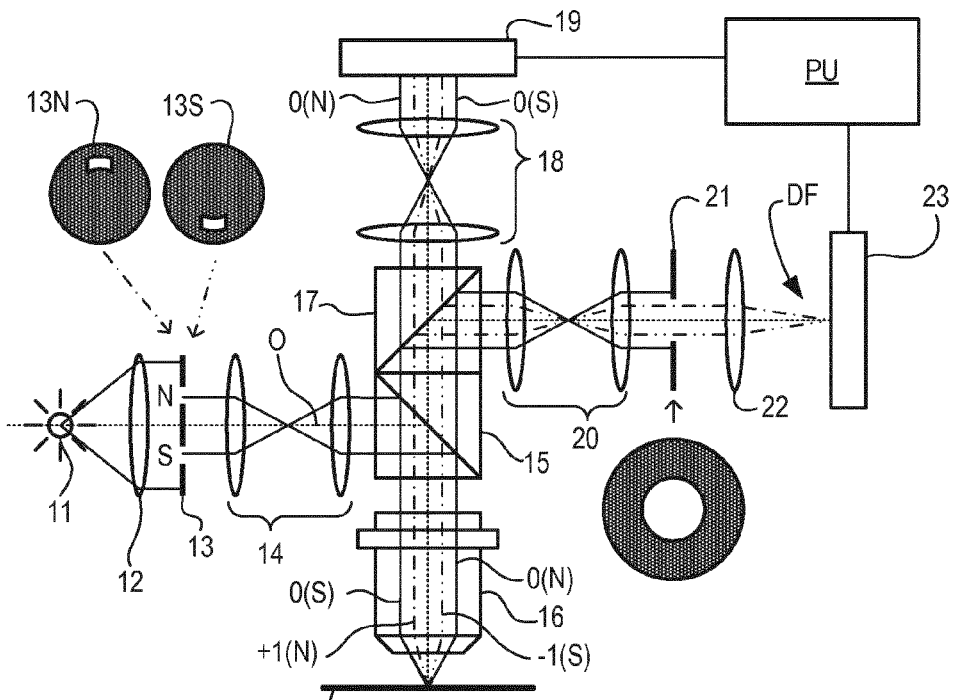
FIG. 3 comprises a schematic diagram of an optical apparatus incorporating a photon source, the apparatus in this example having the form of a scatterometer used in metrology.

FIG. 3 is a schematic diagram of an optical apparatus in the form of a scatterometer suitable for performing metrology in conjunction with the lithocell of FIG. 2. The apparatus may be used for measuring critical dimensions of features formed by lithography, measuring overlay between layers and the like. A product feature or dedicated metrology target is formed on substrate W. The apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 is directed onto substrate W via a beam splitter 15 by an optical system comprising lenses 12, 14 and objective lens 16. These lenses are arranged in a double sequence of a 4F arrangement. A different lens arrangement can be used, provided that it still provides an image of the source on the substrate, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. For example, as illustrated, aperture plate 13 can different forms, two of which are labeled 13N and 13S, allowing different illumination modes to be selected. The illumination system in the illustrated example forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

At least the 0th and one of the −1 and +1 orders diffracted by the target on substrate W are collected by objective lens 16 and directed back through beam splitter 15. A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can be used for many measurement purposes such as reconstruction.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The image detected by sensor 23 is thus referred to as a 'dark-field' image. Note that the term 'image' is used here in a broad sense. An image of the grating lines as such will not be formed, if only one of the −1 and +1 orders is present.

The images captured by sensors 19 and 23 are output to image processor and controller PU, the function of which will depend on the particular type of measurements being performed. More detail of the apparatus and its applications can be found in the prior patent applications mentioned in the introduction above. The present disclosure is concerned with the construction and operation of the light source 11, to provide higher brightness than the Xe arc lamp used in the known apparatus.

Figure 4:
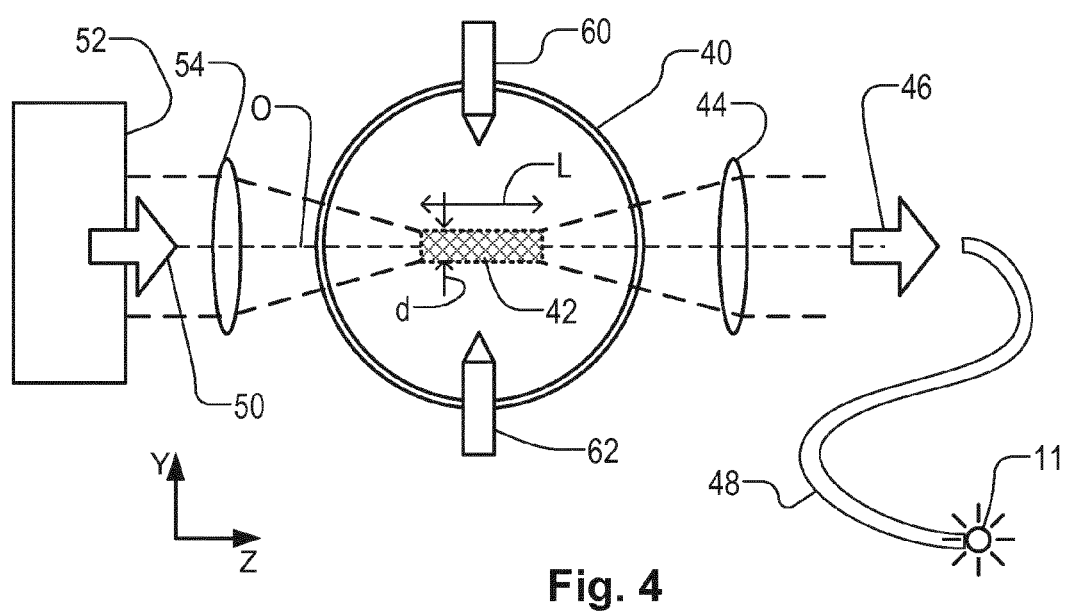
FIG. 4 is a schematic diagram of a photon source used in the apparatus of FIG. 3.

FIG. 4 shows schematically the principal components of a laser-driven photon source apparatus. The central component is a first container 40, for example a glass capsule, containing a predetermined gaseous atmosphere. A suitable gas for example may be xenon (Xe), or a xenon-argon mix. Within this atmosphere, a plasma 42 is generated in a manner to be described, and the plasma emits light (more generally photons of radiation of the desired wavelengths). Collection optics 44 form a beam 46 of the radiation that is coupled to a optical fiber 48. Fiber 48 delivers the radiation to the point where it is needed. When the photon source is used as the source in the apparatus of FIG. 3, the end of fiber 48 forms the source 11 seen in FIG. 3. Collection optics 44 is shown here as a simple lens, but can of course be more complex in practical embodiment. Reflective rather than refractive optics may be used.

Plasma 42 in this embodiment is generated by application of drive radiation 50 which is generated in this example by a laser 52. Drive optics 54 focus the laser which reaches its narrowest point at the location where the plasma 42 is desired to be formed and maintained. The laser 52 may be one of a number of different types of high power laser available today or in future. It may for example be a Nd:YAG laser, a CO2 laser, a diode laser, a fiber laser. Drive optics 54 is shown here as a simple lens, but can of course be more complex in practical embodiment. Reflective rather than refractive optics may be used. Further components may be provided to condition the laser radiation in its profile or spectral characteristics. A beam expander may be used, for example.

The laser radiation may be for example in infrared wavelengths, such as 700 to 2000 nm. The plasma will typically generating radiation at shorter wavelengths in the infrared, visible and/or ultraviolet bands, for example down to 200 nm or below. Among this plasma radiation are the desired wavelengths for use in the metrology apparatus or other application. Filter components 58 may be provided in the optical path, for example to reduce the amount of infrared radiation entering collection optics 44 and/or fiber 48. Such filters can be placed inside and/or outside first container 40. They may also be integrated with the first container wall, and/or with other components of the collection optics 44.

Laser energy 50, although very narrowly focused, is not necessarily sufficient to ignite the plasma from a cold start, and electrodes 60 and 62 are provided with appropriate power and control circuitry (not shown), in order to ignite the plasma. These electrodes may be similar to those used in a conventional gas discharge lamp, but are used only during a start-up phase of operation.

In the diagram, axes X, Y and Z are defined for the sake of this description. The Z axis is aligned with an optical axis O. The Y direction is aligned with the electrodes 60, 62. The X axis is transverse to the electrodes, and normal to the plane of the diagram. The apparatus can be constructed or mounted with these axes in any orientation that is convenient for its application. Note that there is no component obstructing the optical path from the plasma 42 to the collection optics in the Z direction. There is also in this example nothing obstructing the path of light in the X direction (not shown in this view).

It will be noted that plasma 42, or at least the region of the plasma from which the desired radiation is taken, may be elongate in form, having approximately the shape of a cylinder, or cigar. We will refer to the shape as cylindrical for the sake of explanation. The length of the cylinder is L and its diameter is d. The real plasma will comprise a cloud of elongate form, centered on this cylindrical region. Collection optics 44 is arranged with its optical axis O aligned with the longitudinal direction of the plasma, that is the Z direction in this example. The area of the plasma thus appears as $\pi d^2/4$, that is the area of one end of the cylinder. When L is made substantially greater than d, the depth of plasma from which photons can enter the collection optics through this small area is greater, compared with looking at the plasma in a transverse direction. This allows a higher brightness to be seen over that area, for a given size and intensity of plasma. The etendue of an optical source (or receiver) is broadly speaking the product of the area of the source (receiver) and its exit (entrance) angle. The etendue of the collection optics 44, as with any imaging system, is the product of spot size times and the square of its numerical aperture (NA2). The NA in turn is determined by the entrance angle θ. The etendue of the radiating plasma is in general going to be larger than the etendue of the collection optics 44. Collection optics 44 may be focused at a hypothetical source point 64 midway along the cylinder, as illustrated. In practical examples, the length L of light emitting plasma region 42 may be on the order of a millimeter, say 0.5 to 5 mm. The diameter d may be much smaller, in the range of say 0.01 to 2 mm, for example 0.1 to 1 mm.

In practice, the plasma absorbs very little of the wanted radiation, so that photons emitted anywhere along the length L of the cylinder can travel in the entrance cone of collection optics 44 and into fiber 48. Therefore, compared with the transverse direction, the plasma appears brighter (greater luminous flux per unit area per unit solid angle) than when viewed in the transverse direction. Whereas some laser driven light sources, such as described in US 2011/204265 A1, seek to capture light emitted in the transverse direction, the photon source illustrated herein captures light emitted in the longitudinal direction to exploit the enhanced brightness and smaller extent of the plasma. Either capturing arrangement can be used in combination with the novel concepts disclosed herein.

Figure 5:
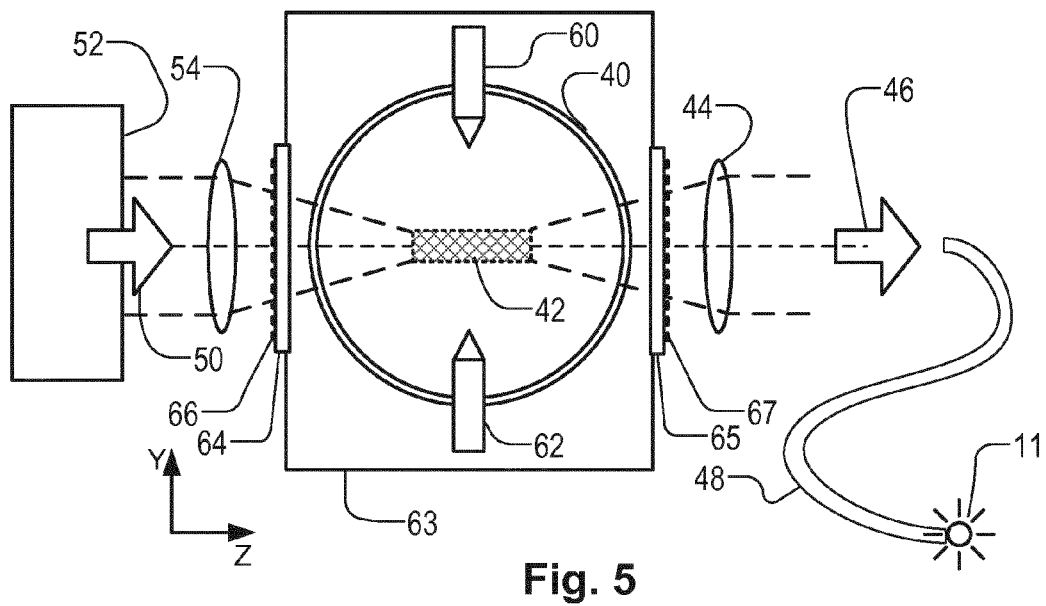
FIG. 5 is a schematic diagram of a photon source apparatus, according to an embodiment of the present invention.

FIG. 5 shows a photon source apparatus according to an embodiment of the invention. Note that plasma generation/ excitation and collection/transport of the subsequent radiation follow the same structure and process as previously described in relation to FIG. 4.

FIG. 5 shows a second container 63 enclosing a photon source represented, in this example, by the laser-driven photon source described above (i.e. first container 40, electrodes 60, 62 and appropriate power and control circuitry (not shown)). Second container 63 is an airtight (hermetically sealed) container, which may enclose an atmosphere of air, or any other fluid that has the desired optical properties. Second container 63 also comprises at least one light transmitting element, e.g. light transmitting windows 64, 65, and, at least one filter component, e.g. filter components 66, 67. It should be appreciated that the photon source does not necessarily have to take the form of that depicted and may take any other suitable form.

Drive radiation 50 may be focused by focusing optics 54 onto plasma 42, entering the second container 63 via window 64. Light generated by plasma 42 may exit the second container 63 via window 65, to be collected by collection optics 44. Filter components 66 block ultraviolet radiation exiting the second container 63 through window 64. Filter components 67 may also block ultraviolet and infrared radiation exiting second container 63 through window 65.

Windows 64 and 65 should be airtight and made of suitable coated/uncoated materials. The windows may also be any size, shape or thickness and/or may be flat/curved. Similarly, filter components 66, 67 may be provided in the optical path and made of suitable materials with variable thickness, fixed by the required wavelengths. The filters can be placed inside and/or outside second container 63. Filters 66, 67 may be integrated with the windows 64, 65, for example they may comprise coating layers on windows 64, 65. Filter components 67 may also be integrated with other components of the collection optics 44.

Collection optics 44 may be placed inside second container 63. In this configuration, the light may exit second container 63 through fiber 48 connected to second container 63.

Airtight second container 63 and contents may be assembled in any relatively clean environment, e.g. in a typical laboratory environment, and is not required to be assembled in a cleanroom. The second container 63 need only be filled with air and does not necessarily need filling with an inert gas. Air has the advantage of being the cheapest fluid and also is the easiest to handle. However, if other fluids are used, the hermetic seal provides protection from chemical contamination entering from outside of the second container.

The walls of airtight second container 63 may be made of suitable materials which are able to block unwanted radiation (or all radiation), for example, materials which block UV radiation generated by the enclosed photon source. Furthermore, second container 63 may be of any dimension, shape and wall thickness to meet the application requirements. The volume of the second container 63 may be as small as possible in order such that the total amount of generated chemicals is relatively small. Consequently the second container 63 may be only a little larger than the first container 40. For example it may be that the volume of the second container is no larger than 200%, 150% or 120% than that of the first container. In other embodiments the second container 63 may be somewhat larger (in the order of 100× greater volume compared to a first container 40 having a volume in the order of 10000 $m^3$) so as to increase its surface area and aid cooling.

Since the second container 63 is airtight, and providing that ultraviolet light is filtered out from the output radiation 46 (for example at windows 64, 65), ozone produced by the ultraviolet light remains encapsulated in second container 63. In addition, because of the second container 63 is airtight, no extra chemicals can be enter the second container 63 during the lifetime of the photon source.

In one embodiment, the first container 40 and the second container 63 comprise a single replaceable unit, which can be replaced on failing in a similar manner to bulb replacement (i.e. replacement of container 40) in an apparatus such as that depicted in FIG. 4.

The use of the photon source apparatus as disclosed herein dispenses with the need to purge systems, or the use of ozone-free lamps having a shorter lifetime than other lamps. The first container 40 instead simply transmits most or all of the ultraviolet radiation generated by the plasma. Consequently, costs are significantly reduced and efficiency improved.

It is common for design measures to be taken to try and reduce the length L of the plasma to concentrate its power in a smaller length, the constraints on the plasma shape in the source are relatively relaxed. Whereas, in some prior examples in, the plasma extends longitudinally in what is depicted as the Y direction, between the igniting electrodes, in the illustrated source the plasma in normal operation is arranged so that rays in the longitudinal direction are not obscured, and can be captured by the collection optics 44. Similarly, while in other prior examples the plasma extends in what is depicted as the Z direction, this is obscured by the driving laser optics, and the usable light is captured by a curved mirror, after being emitted in the X and Y directions from the plasma. Thus many prior examples rely on capturing the photons emitted transversely from the plasma. While embodiments of the invention may also rely on capturing the photons emitted transversely from the plasma, it can be shown that improved performance can be obtained using arrangements such as those illustrated in FIGS. 5 to 7.

Figure 6:
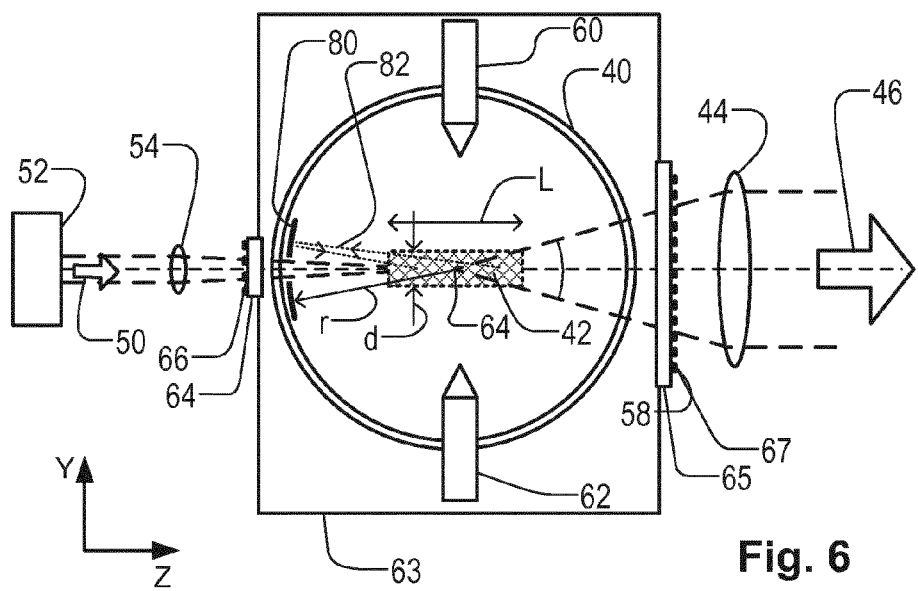
FIG. 6 is a schematic diagram of a photon source used in the apparatus of FIG. 3 according to a second embodiment of the present invention.
Figure 7A:
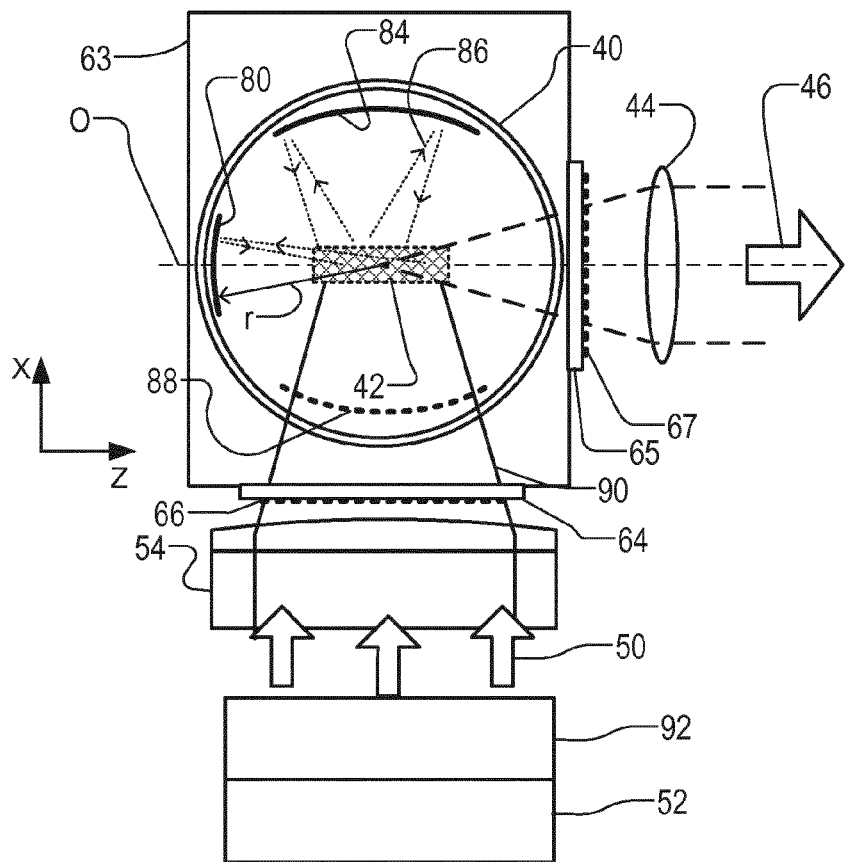
FIGS. 7 (a) and (b) are schematic views of a photon source used in the apparatus of FIG. 3 according to a third embodiment of the present invention.
Figure 7B:
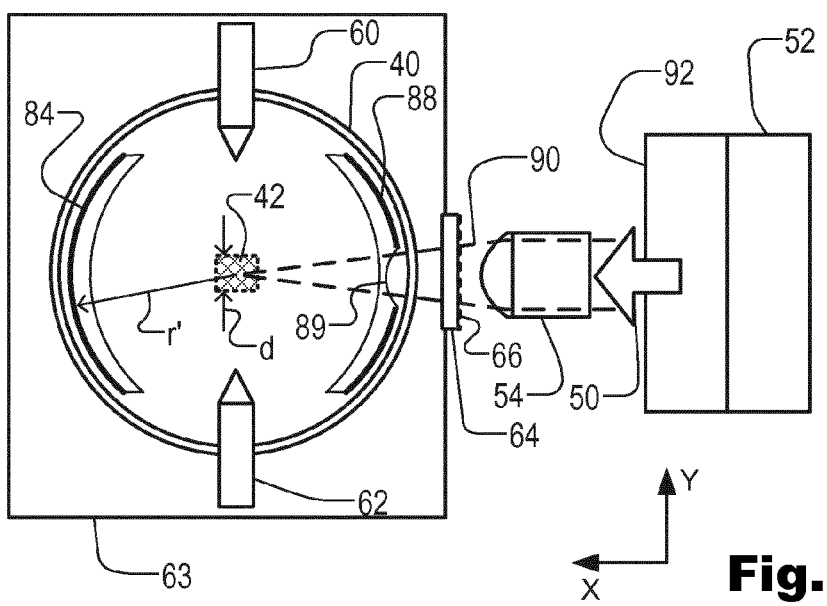

It should be noted that the intensity profile of the radiation emitted by the plasma source might not be perfectly uniform across the field of view of collection optics 44. While constraints on the plasma dimensions are relaxed as described above, still the entrance NA of collection optics 44 should be reasonably uniformly filled with radiation. The larger the aspect ratio L/d of the plasma, the smaller the etendue will be in which the radiation is uniformly distributed. Mixing of the light to make it more homogeneous may be desired, for example when the photon source apparatus is used to deliver a homogeneous light field across aperture 13 in the apparatus of FIG. 3. Sufficient mixing may occur naturally within the fiber 48, or additional measures may be taken. Also, optical properties of the walls of the first container 40 should be good enough at the key locations that they do not degrade the quality of the drive laser beam or the pencil of rays emanating from plasma 42 to collection optics 44. Optical properties of the first container wall, as well as windows 64, 65 and filters 66, 67, should of course be taken into account in designing and setting up the collection optics 44 and focusing optics 54. Functional elements of collection optics 44 and focusing optics 54 can be placed inside first container 40 if desired, and/or may be integrated with the wall of the first container FIGS. 6 and 7 illustrate further embodiments based on the principles just described. The same reference signs are used as in FIG. 5, for components having the same functions. Fiber 48 is omitted from FIGS. 6 and 7 simply to create space. The options and properties described for the example of FIG. 5 apply equally in the examples of FIGS. 6 and 7, unless otherwise stated.

In FIG. 6, the arrangement is very similar to that of FIG. 5, except that a back-reflector 80 is provided to reflect rays 82 emitted in the reverse longitudinal direction back into the plasma. Reflector 80 may be spherical, for example, with curvature centered with radius r on the point of focus 64. As the reverse longitudinal direction is also the direction of the incoming laser beam 50, reflector 80 is formed with an aperture of a suitable size to admit the laser beam. Reflector 80 can be provided inside or outside first container 40, and may be formed on the wall of the first container 40 itself. Additional reflectors may be provided to capture transversely-emitted photons and return them to the plasma. Examples of these will be illustrated in the example of FIG. 7. Photons reflected by these side reflectors will not enter the collection optics which has the small etendue as described. However, they may assist laser energy 50 to maintain the plasma, and they may improve homogeneity of the plasma and hence of the emitted radiation. As before, filter 58 or equivalent components may be provided to tailor the spectral properties of the outgoing radiation beam 46. In particular, a filter 58 may be provided to reduce or eliminate radiation 50 from the laser, for example infrared radiation, entering collection optics 44.

FIG. 7 shows two views of a further modified embodiment. The form and orientation of plasma 42 and collection optics 44 are the same as in the previous examples, and a back-reflector 80 is again provided. In this example, however, the laser radiation 50 that drives the plasma is delivered transversely to the elongate plasma, for example in the X direction. An additional 'side' reflector 84 may be provided to capture transversely-emitted photons 86 and return them to the plasma. An opposite side reflector 88 may be provided, with an aperture 89 for admitting the laser radiation that is delivered by focusing optics 54 in a beam 90. Photons reflected by these side reflectors will not enter the collection optics which has the small etendue as described. However, they may assist laser energy 50 to maintain the plasma, and they may improve homogeneity of the plasma and hence of the emitted radiation. Reflectors 84 and 88 may be spherical, cylindrical or a compound of the two, depending on whether some redistribution (mixing) of energy is required in the longitudinal direction. Reflector 84 may be provided with an aperture similar to that in reflector 88, in order to allow an exit of the laser radiation. Side reflectors can be positioned close to the electrode locations, if desired. As before, reflectors may be inside the first container 40 (as illustrated) or outside it (but within second container 63). They may be integrated with the first container wall.

Instead of being focused into an elongate beam aligned with the longitudinal direction, the laser radiation 50 in this example is spread and focused into a beam 90 having a line-shaped focus, matching the dimensions of the desired plasma 42. To do this, focusing optics 54 comprises primarily a cylindrical lens, as illustrated, to form a convergent beam 90 as seen in FIG. 7 (b), viewing along the Z direction. A beam expander 92 may be provided between laser 52 and optics 54 in order to spread the beam to a desired width. Viewed in the Y direction, as shown in FIG. 7 (a), beam 90 may be convergent as shown. Alternatively, beam 90 may be divergent viewed in the Y direction and convergent viewed in the Z direction. Multiple laser beams and lenses may be deployed to create the desired focusing along the line of plasma 42. Driving radiation could be delivered both transversely and longitudinally, if desired, combining features of FIGS. 5, 6 and 7 together.

In this second example, although the focusing optics may be more complicated, there are some benefits compared with the examples of FIGS. 5 and 6. As a matter of principle, it will be seen that the longitudinal direction of the plasma, which is also the exit direction for the usable radiation, is orthogonal to the axis of the igniting electrodes, which in turn is orthogonal to the axis of entry of the driving laser beam. Therefore this arrangement has greater freedom from the constraints of mechanical and optical interference between these subs-systems. One benefit for example is that back reflector 80, if provided, needs no aperture. Alternatively, a second collection optics and a second output could be taken from the 'back' end of the plasma. The requirement for filtering to prevent the laser radiation entering collection optics 44 is also eliminated or reduced. Other variations and modifications discussed in the context of the earlier examples can be applied in the FIG. 7 example also.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. As already mentioned, the invention may be applied in industrial processing applications quite separate from lithography. Examples might be in production of optical components, automotive manufacture, construction—any number of applications where object data exists in the form of measurements made with a certain spatial distribution over the product. As in the example of lithography. the set of measurements that is subjected to multi-variate analysis can be measurements made for different product units, and/or different instances of measuring the same product units. Although specific reference may have been made above to the use of embodiments of the invention in the context of optical lithography, it will be appreciated that the invention may be used in other types of lithography, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams. As mentioned above, the term radiation in the context of the driving system may also encompass microwave radiation.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiment, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A radiation produced plasma-based photon source apparatus, comprising:
   a first container configured to contain a medium in which a plasma is generated following excitation by a driving radiation, where the plasma is in an elongate form having a length along a longitudinal axis that is substantially greater than its diameter in a direction transverse to the longitudinal axis, and
   a second container configured to enclose the first container,
   wherein the first container is operable to emit output radiation, the output radiation emerging from one end of the plasma along the longitudinal axis, and the output radiation further comprising an ultraviolet component;
   wherein the output radiation is directed out of the first and second containers along the longitudinal axis; and
   wherein the second container is operable to substantially remove the ultraviolet component from the output radiation.

2. The photon source apparatus as claimed in claim 1, wherein the second container encloses no more than the first container, electrical connections, and an atmosphere.

3. The photon source apparatus as claimed in claim 2, wherein the atmosphere comprises air.

4. The photon source apparatus as claimed in claim 1, wherein the second container comprises a light transmitting element, operable to transmit at least some of the output radiation.

5. The photon source apparatus as claimed in claim 1, wherein the second container comprises a light transmitting element, operable to transmit the driving radiation to generate the plasma.

6. The photon source apparatus as claimed in claim 1, wherein the second container comprises a filter element being operable to substantially remove the ultraviolet component from the output radiation.

7. The photon source apparatus as claimed in claim 6 wherein the filter element is operable to substantially remove an infrared component from the output radiation.

8. The photon source apparatus as claimed in claim 1, wherein the second container comprises a filter element being operable to substantially remove an ultraviolet component from the driving radiation.

9. The photon source apparatus as claimed in claim 1, wherein the first container does not substantially remove the ultraviolet component from the output radiation.

10. The photon source apparatus as claimed in claim 1, wherein the first and second containers form a single integrated apparatus replaceable as a single unit following failure.

11. The photon source apparatus as claimed in claim 1, further comprising:
    a driving system configured to generate the driving radiation and to form the driving radiation into at least one beam focused on a plasma forming zone within the first container, and
    a collecting optical system configured to collect photons emitted by the plasma maintained by the radiation beam at the plasma location and to form the collected photons into the output radiation.

12. The photon source apparatus as claimed in claim 11, wherein:
    the driving system is configured to maintain the plasma in the elongate form, and
    the collecting optical system is configured to collect photons emerging from one end of the plasma along the longitudinal axis.

13. The photon source apparatus as claimed in claim 11 wherein the driving system includes at least one laser for generating the beam of radiation.

14. The photon source apparatus as claimed in claim 11 wherein the driving radiation has wavelengths predominantly in a first range comprising infrared wavelengths and the output radiation has wavelengths predominantly in a second range different from the first range, the second range comprising visible and/or ultraviolet radiation.

15. The photon source apparatus as claimed in claim 11, wherein the driving system is arranged to deliver the driving radiation along the longitudinal axis at an end of the plasma opposite to the end from which the collected photons emerge.

16. The photon source apparatus as claimed in claim 11, wherein the driving system is arranged to deliver the driving radiation to the plasma forming location in a direction transverse to the longitudinal direction.

17. The photon source apparatus as claimed claim 16, wherein the driving system is arranged to focus the driving radiation into a substantially line focus corresponding to the elongated form of the plasma.

18. The photon source apparatus as claimed in claim 11, further including two or more electrodes positioned on opposite sides of the plasma forming location, for use in igniting the plasma prior to operation, the electrodes being placed away off the longitudinal axis.

19. The photon source apparatus as claimed claim 18 wherein the electrodes are positioned on an axis orthogonal to the longitudinal axis.

20. The photon source apparatus as claimed claim 19 wherein the electrodes, the driving system and the collecting optical system are arranged on three axes that are mutually orthogonal.

21. The photon source apparatus as claimed in claim 11, further comprising a reflector positioned and shaped to reflect back into the plasma photons emerging in a longitudinal direction from an opposite end of the plasma.

22. The photon source apparatus as claimed in claim 11, further comprising one or more reflectors positioned and shaped to reflect back into the plasma photons emerging in one or more directions transverse to the longitudinal direction of the plasma.

23. A method of measuring a property of structures that have been formed by a lithographic process on a substrate, the method comprising:
  directing driving radiation into a first container enclosed in a second container, the first container containing a medium to generate a plasma, the plasma being in an elongate form having a length along a longitudinal axis that is substantially greater than its diameter in a direction transverse to the longitudinal axis;
  emitting output radiation from the first container, the output radiation emerging from one end of the plasma along the longitudinal axis and the output radiation further comprising an ultraviolet component;
  directing the output radiation out of the first and second containers along the longitudinal axis;
  substantially removing the ultraviolet component from the output radiation using the second container;
  illuminating the structures using the output radiation;
  detecting radiation diffracted by the structures; and
  determining from properties of the diffracted radiation one or more properties of the structure.

24. An inspection apparatus for measuring a property of a structure on a substrate, the apparatus comprising:
  a support configured to support the substrate having the structure thereon;
  an optical system configured to illuminate the structure under predetermined illumination conditions and to detect predetermined portions of radiation diffracted by the component target structures under the illumination conditions;
  a processor arranged to process information characterizing the detected radiation to obtain a measurement of the property of the structure,
    wherein the optical system includes a photon source apparatus comprising:
      a first container containing a medium in which a plasma is generated following excitation by a driving radiation, where the plasma is in an elongate form having a length along a longitudinal axis that is substantially greater than its diameter in a direction transverse to the longitudinal axis, and
      a second container enclosing the first container,
      wherein the first container is operable to emit output radiation, the output radiation emerging from one end of the plasma along the longitudinal axis, and the output radiation further comprising an ultraviolet component; and
      wherein the output radiation is directed out of the first and second containers along an axis that runs through the longitudinal axis;
      wherein the second container is operable to substantially remove the ultraviolet component from the output radiation.

25. A lithographic system comprising:
  a lithographic apparatus comprising:
    an illumination optical system arranged to illuminate a pattern;
    a projection optical system arranged to project an image of the pattern onto a substrate; and
  an inspection apparatus comprising:
    a support configured to support the substrate having the structure thereon;
    an optical system configured to illuminate the structure under predetermined illumination conditions and to detect predetermined portions of radiation diffracted by the component target structures under the illumination conditions;
    a processor arranged to process information characterizing the detected radiation to obtain a measurement of the property of the structure,
    wherein the optical system includes a photon source apparatus comprising:
      a first container containing a medium in which a plasma is generated following excitation by a driving radiation, where the plasma is in an elongate form having a length along a longitudinal axis that is substantially greater than its diameter in a direction transverse to the longitudinal axis, and
      a second container enclosing the first container,
      wherein the first container is operable to emit output radiation, the output radiation emerging from one end of the plasma along the longitudinal axis, and the output radiation further comprising an ultraviolet component; and
      wherein the output radiation is directed out of the first and second containers along an axis that runs through the longitudinal axis;
      wherein the second container is operable to substantially remove the ultraviolet component from the output radiation,
    wherein the lithographic apparatus is arranged to use the measurement results from the inspection apparatus in applying the pattern to further substrates.

26. A method of manufacturing devices wherein a device pattern is applied to a series of substrates using a lithographic process, the method comprising:
  inspecting at least one composite target structure formed as part of or beside the device pattern on at least one of the substrates using a method comprising:
    directing driving radiation into a first container enclosed in a second container, the first container containing a medium to generate a plasma, the plasma being in an elongate form having a length along a longitudinal axis that is substantially greater than its diameter in a direction transverse to the longitudinal axis;
    emitting output radiation from the first container, the output radiation emerging from one end of the plasma along the longitudinal axis and the output radiation further comprising an ultraviolet component;

directing the output radiation out of the first and second containers along the longitudinal axis;

substantially removing the ultra violet component from the output radiation using the second container;

illuminating the structures using output radiation of a photon source apparatus;

detecting radiation diffracted by the structures; and determining from properties of the diffracted radiation one or more properties of the structure; and controlling the lithographic process for later substrates in accordance with the result of the inspection method.

\* \* \* \* \*